United States Patent [19]

Hajos et al.

[11] 4,276,216

[45] Jun. 30, 1981

[54] SYNTHESIS OF DIOXABICYCLO[3.2.1]OCTANES AND OXEPANES

[75] Inventors: Zoltan G. Hajos, Princeton; Michael P. Wachter, Bloomsbury, both of N.J.

[73] Assignee: Ortho Pharmaceutical Corporation, Raritan, N.J.

[21] Appl. No.: 174,070

[22] Filed: Jul. 31, 1980

[51] Int. Cl.$^3$ .................................................. C07D 319/10
[52] U.S. Cl. ............................ 260/340.6; 260/333; 260/347.8; 260/348.25; 260/348.48; 556/482; 568/418

[58] Field of Search ....................................... 260/340.6

[56] References Cited

U.S. PATENT DOCUMENTS

| | | | |
|---|---|---|---|
| 2,322,821 | 6/1943 | Brown | 260/340.6 |
| 2,771,471 | 11/1956 | De Groote | 260/340.6 |

*Primary Examiner*—Ethel G. Love
*Attorney, Agent, or Firm*—Benjamin F. Lambert

[57] ABSTRACT

The synthesis of C-4 alkyl analogs of racemic (1RS,4SR,5RS)-4-(4,8-dimethyl-5-hydroxy-7-nonenyl)-4-methyl-3,8-dioxabicyclo[3.2.1]octane-1-acetic acid and the corresponding (1RS,4RS,5RS)- derivative is described. The dioxabicyclo[3.2.1]octanes are useful as contragestational agents.

13 Claims, No Drawings

SYNTHESIS OF DIOXABICYCLO[3.2.1]OCTANES AND OXEPANES

The synthesis of optically active 4-(4,8-dimethyl-5-hydroxy-7-nonenyl)-4-methyl-3,8-dioxabicyclo[3.2.1]octane-1-acetic acid (I)

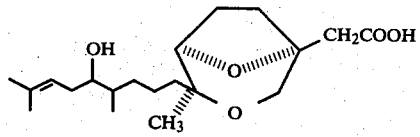

I from an optically active component of the zoapatle plant is described in U.S. Pat. No. 4,102,895. The present invention relates to the C-4 alkyl analogs of racemic (1RS,4SR,5RS)-4-(4,8-dimethyl-5-hydroxy-7-nonenyl)-4-methyl-3,8-dioxabicyclo[3.2.1]octane-1-acetic acid and the corresponding (1RS,4RS,5RS) derivative and to a method of synthesizing the C-4 alkyl analogs. The novel C-4 alkyl analogs which are the subject of this invention have the following chemical configuration.

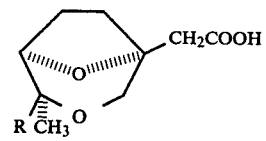

II wherein R is a straight or branched chain alkyl group of from 1–12 carbon atoms such as ethyl, n-propyl, isopropyl, n-butyl, isobutyl, pentyl, hexyl, octyl, nonyl, n-decyl, dimethyl decyl and the like, and the pharmaceutically acceptable acid addition salts thereof. The C-4 alkyl analogs of racemic (1RS,4SR,5RS)-4-(4,8-dimethyl-5-hydroxy-7-nonenyl)-4-methyl-3,8-dioxabicyclo[3.2.1]octane-1-acetic acid are active as contragestational agents. The novel dioxabicyclo[3.2.1]octanes are prepared by a synthetic route comprised of several steps which are summarized in the following schematic diagram:

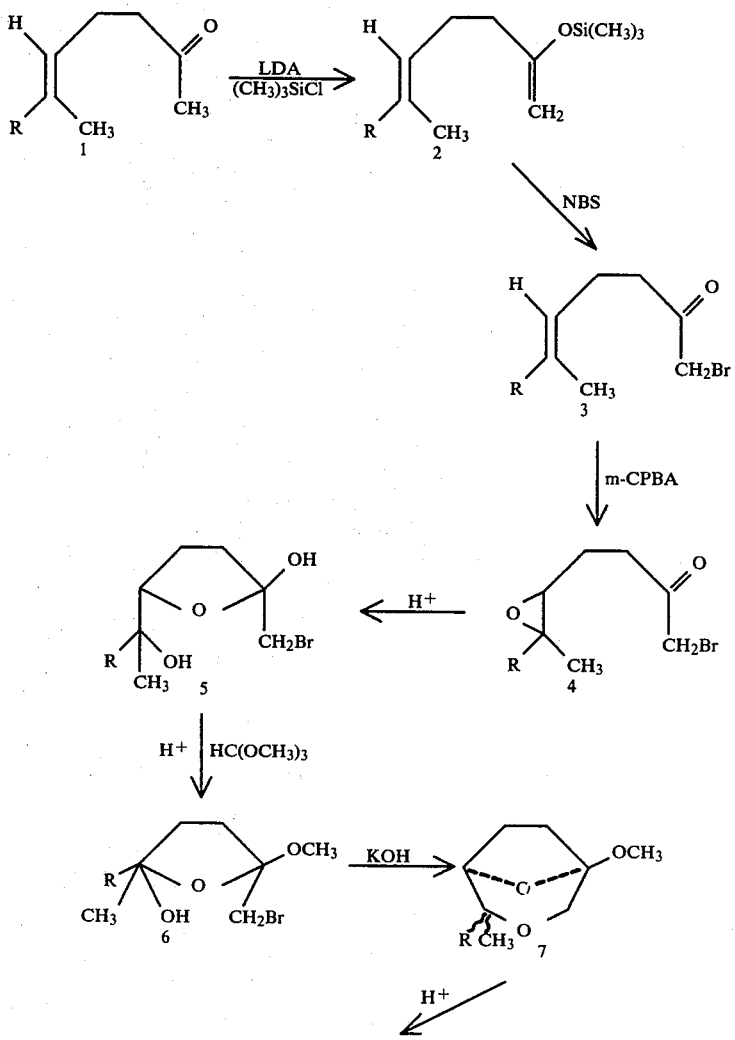

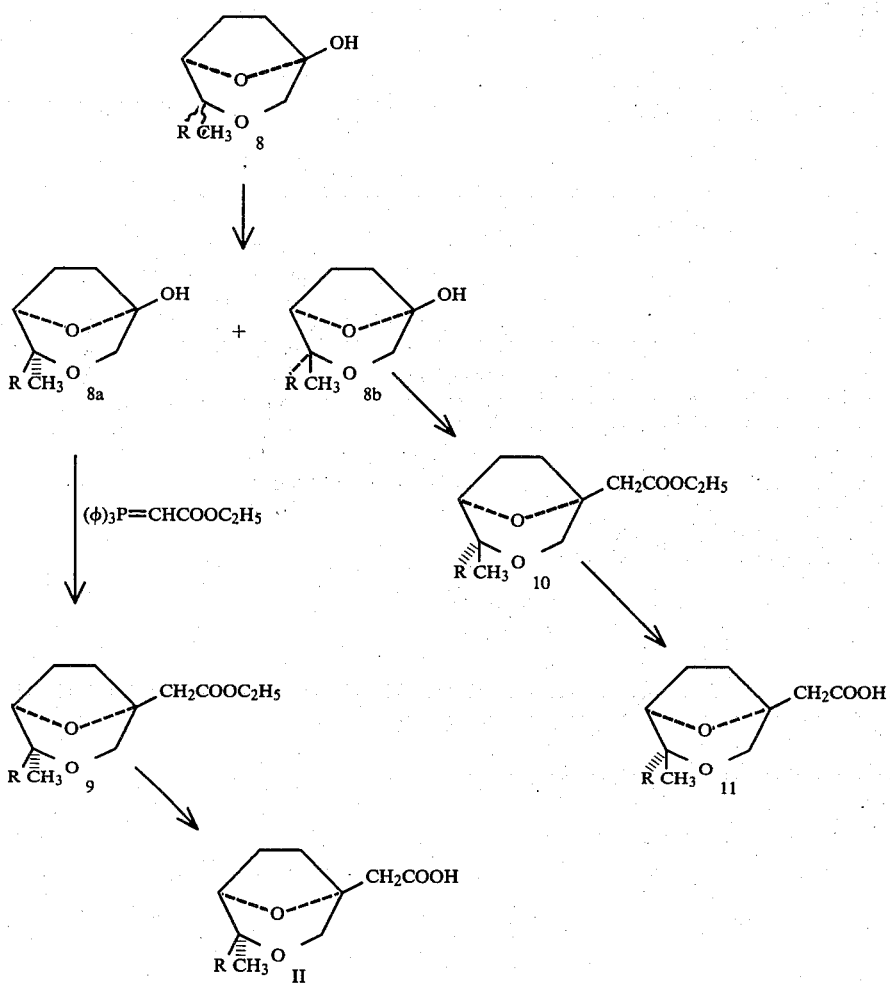

wherein R is a straight or branched chain alkyl group of from 1–12 carbon atoms, LDA is lithium diisopropylamide; NBS is N-bromosuccinimide; and m-CPBA is m-chloroperbenzoic acid.

The first step in the synthesis of the bicyclic acid (II) involves the conversion of the unsaturated ketone (1) to the silyl enol ether (2). The conversion is carried out by first reacting the ketone with lithium diisopropylamide in a suitable solvent such as tetrahydrofuran, dimethoxyethane and dioxane. The reaction is carried out a temperature between −80° C. and +20° C. The preferred temperature range is between −70° and 0° C. The resulting enolate is then reacted with a trialkylsilyl halide such as, for example, trimethylsilyl chloride in the presence of a mild base such as triethylamine or pyridine. The reaction product (2) is obtained by techniques known to those skilled in the art. The silyl enol ether (2) is then brominated with a brominating agent such as N-bromosuccinimide, for example, to give the bromo-ketone (3). The reaction is carried out in a suitable solvent such as tetrahydrofuran, dimethoxyethane and dioxane at a temperature between −80° C. and 0° C. The preferred reaction temperature is about −78° C. Epoxidation of the bromoketone (3) with a peracid such as m-chloroperbenzoic acid, perbenzoic acid, monoperphthalic acid, peracetic acid and trifluoroperacetic acid in a suitable solvent such as, for example, methylene chloride, chloroform, ether and dichloroethane gives the epoxide (4) which is converted to the hemiketal (5) upon treatment with dilute acid in a suitable solvent. Acids which may be employed include dilute hydrochloric acid, perchloric acid, phosphoric acid and sulfuric acid. As the solvents acetone, butanol and tetrahydrofuran may be employed. The hemi-ketal (5) is then converted to the ketal (6) by treatment with a trialkylorthoformate such as, for example, trimethylorthoformate and triethylorthoformate and a weakly acidic alcoholic solution. Acids such as sulfuric acid, hydrochloric acid and phosphoric acid may be employed. Cyclization of the ketal (6) with an alkali metal hydroxide or oxide such as potassium hydroxide, sodium hydroxide, potassium tert. butoxide or sodium methoxide or with a metal hydride such as sodium hydride, in a suitable solvent such as dimethyl sulfoxide, dimethylformamide or tetrahydrofuran-hexamethylphosphoramide gives the bicyclic oxido-oxepane (7).

The ketal protecting group is removed from the oxido oxepane by reaction with dilute acid such as aqueous hydrochloric acid, sulfuric acid or acetic acid to give a mixture of epimeric hemi-ketals (8a and 8b). The epimers can be separated by physical means such as chromatography, for example, to give the desired 1RS,4RS,5SR epimer (8a) and the 1RS,4SR,5SR epimer (8b). When the series of reactions is carried out on the unsaturated ketone (1) having the E-configuration only the hemi-ketal having the 1RS,4RS,5SR configuration is obtained. The hemi-ketal (8a) is then converted to the bicyclic ester (9) by reaction with a carbalkoxymethylene-triphenylphosphorane such as carbethoxymethylenetriphenylphosphorane for example. The reaction is preferably carried out at elevated temperatures in an inert atmosphere such as nitrogen. When the reaction is carried out at elevated temperatures, a temperature ranging from 50° to 120° C. may be employed. The preferred temperature range is 90°-120° C. The bicyclic ester is then hydrolyzed to the corresponding acid (II) by techniques known to those skilled in the art. The hydrolysis reaction is preferably carried out with an alkali metal or alkaline earth metal base such as sodium hydroxide, potassium hydroxide and calcium hydroxide in an aqueous or alcoholic aqueous solution at a temperature between about 0° C. and 20° C. In a similar fashion, the corresponding epimer (8b) is converted to the free acid (11). The free acid (II) and the esters are useful as contragestational agents.

The unsaturated ketone (1) which is used as the starting material is prepared as a mixture of isomers (E:Z) from 2-heptanone by the method of Kovalev [Kovalev, B. G. et al. *Zh.Org. Khim.*, 11, 1183-87 (1975)]. Alternatively, the pure E isomer can be synthesized by the method described in co-pending application Ser. No. 49,760 filed June 18, 1979.

The hemi-ketal (8a) can be converted to the 3-alkyloxy-6-oxo-oxepane according to the following scheme:

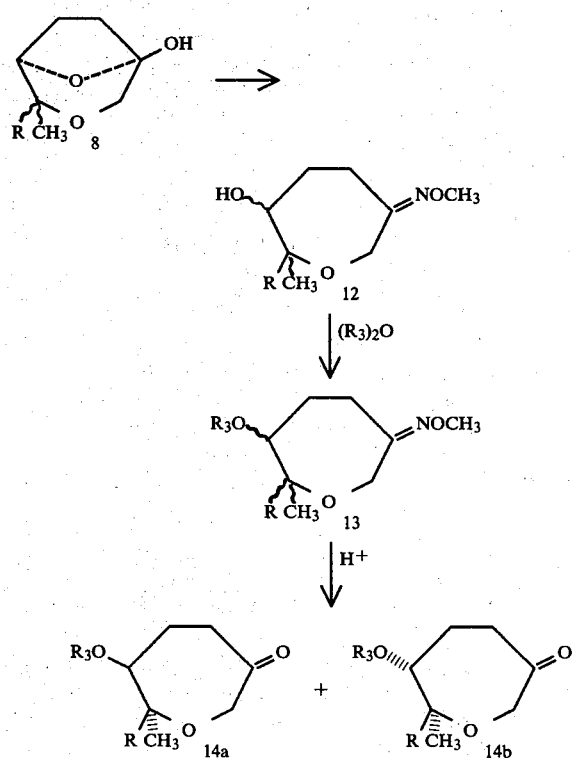

wherein R is as previously defined and R₃ is an alkanoyl group having 2-5 carbon atoms.

In the first step in the preparation of the oxepane analog the hemi-ketal is first treated with a mild base such as potassium acetate in a suitable solvent such as methanol and then reacted with methoxylamine hydrochloride to form the alcohol (12). The alcohol is then converted to the ester (13) by acylation with an acylating agent such as acetic anhydride, propionic anhydride and butyric anhydride in the presence of a base such as pyridine. Reaction of the ester derivative with dilute acid, such as for example hydrochloric acid, gives the 3-alkyloxy-6-oxo-oxepane analog (14a and 14b) in the form of C-3 -isomers. The C-3 isomers can be separated by the chromatographic method described in copending application Ser. No. 141,524 filed Apr. 18, 1980. The oxepane analogs are useful as intermediates in the preparation of zoapatanol and its analogs.

The invention is further described in the following examples of more preferred embodiments thereof which are presented for the purpose of illustration and not by way of limiting the scope of the invention.

EXAMPLE 1

6-Methyl-2-trimethylsiloxy-undec-1,5-diene (2)

Triphenylmethane indicator (50 mg) is added to isopropylamine (9.15 ml, 0.065 moles) in anhydrous tetrahydrofuran (80 ml). The solution is cooled to 0° C. and a solution of n-butyllithium (2.34 m) in hexane (28.5 ml, 0.065 moles) is added carefully while stirring at 0°-5° C. The mixture is kept at 0° C. for 20 minutes and then cooled to −70° C. 6-Methyl-2-oxo-5-undecene (9.1 g, 0.05 moles, 60:40 E:Z mixture) is dissolved in anhydrous tetrahydrofuran (9.0 ml.) and added to the above solution of lithium diisopropylamide in tetrahydrofuran while stirring at −70° C. within 15 minutes (−70°-65° C.). To the resultant enolate solution is added immediately at −70° C. while stirring a freshly prepared and centrifuged solution of trimethylsilyl chloride (15 ml, ~0.12 moles) and triethylamine (4.0 ml, ~0.029 moles) in tetrahydrofuran (25 ml). The solution is kept at −70° C. for 1.5 hours. Solid sodium bicarbonate (10 g) is added. The solution is then allowed to come to −10° C., and a saturated aqueous sodium bicarbonate solution (60 ml) is added. The solution is then allowed to come to room temperature, the tetrahydrofuran layer is separated, and the aqueous layer is re-extracted with ether. The combined organic extract is washed with saturated aqueous chloride solution, dried with sodium sulfate, filtered, and evaporated in vacuo. Drying in high vacuo gives crude 6-methyl-2-trimethylsiloxy-undec-1,5-diene (13.75 g).

IR (neat): 1640-1660 cm$^{-1}$ (enol silyl ether);

NMR (CDCl₃) δ5.15 (m, 1H, —$\underline{H}$C=CH₂), 4.07 (s, 2H, —C=C$\underline{H}_2$), 1.70, 1.62 [2×s, 3H total, (40/60 Z:E), $\underline{H}_3$—C=CH—], 0.90 [dist'd t, 3H, C$\underline{H}_3$—(CH₂)₄—].

GC/MS=two fractions (~40/60 ratio), showing identical mass spectra. M⁺ 252, M—CH₃=239, M—nC₅H₁₁=183.

When in the above procedure 6-methyl-2-oxo-5-nonene and 6-methyl-2-oxo-5-decene are employed in place of 6-methyl-2-oxo-5-undecene, the corresponding 6-methyl-2-trimethylsiloxy-non-1,5-diene and 6-methyl-2-trimethylsiloxy-dec-1,5-diene are obtained.

EXAMPLE 2

1-Bromo-6-methyl-2-oxo-undec-5-ene (3)

Anhydrous solid sodium bicarbonate (5.0 g) is added to crude 6-methyl-2-trimethylsiloxy-undec-1,5-diene (13.75 g, max. 0.05 moles) dissolved in tetrahydrofuran (150 ml). The mixture is cooled to −78° C. under argon and stirred. Solid N-bromosuccinimide (9.1 g, ~0.05 moles) is added within 5 minutes with the exclusion of light and moisture.

The reaction mixture is stirred at −78° C. for 2 hours and then cannulated into a stirred mixture of an ice cold 10% aqueous sodium bicarbonate solution and ether. The organic layer is separated, washed with 10% aqueous sodium bicarbonate solution then with saturated aqueous sodium chloride. The solution is dried with sodium sulfate, filtered, and evaporated in vacuo. Drying in high vacuo gives 1-bromo-6-methyl-2-oxo-undec-5-ene (13.05 g).

IR (neat): 1710 cm$^{-1}$ (CO of ketone):
NMR (CDCl$_3$) δ5.07 (m, 1H, HC=CH$_2$—), 3.90 (s, 2H, —CO—CH$_2$—Br), 1.72, 1.67 [2×s, 3H total, (40/60 Z:E), H$_3$C=CH—], 0.89 [dist'd t, 3H, CH$_3$(CH$_2$)$_4$—].
GC/MS=two fractions (∼40/60 ratio), showing identical mass spectra M$^+$ 260, M—Br=181, BP 55.

When in the above procedure 6-methyl-2-trimethyl-siloxyocta-1,5-diene and 6-methyl-2-trimethylsiloxyhept-1,5-diene are employed in place of 6-methyl-2-trimethylsiloxyundec-1,5-diene, the corresponding 1-bromo-6-methyl-2-oxo-oct-5-ene and 1-bromo-6-methyl-2-oxo-hept-5-ene are obtained.

EXAMPLE 3

1-Bromo-5,6-epoxy-6-methyl-undecan-2-one (4)

1-Bromo-6-methyl-2-oxo-undec-5-ene (10.4 g, 0.04 mole) is dissolved in methylene chloride (100 ml). The solution is cooled to 0° C. and m-chloroperbenzoic acid (7.9 g, 0.04 mole of 85% pure substance) in methylene chloride (180 ml) is added while stirring at +5°–10° C. within 25 minutes. After stirring for 3 hours at 0° C., the reaction mixture is stored at +5° C. for 16 hours. It is then filtered through a sintered glass funnel, and the filtrate is washed first with saturated aqueous sodium bicarbonate, and then 5 times with sodium sulfite (60 g in 500 ml of H$_2$O). The solution is washed with saturated aqueous sodium chloride, dried with sodium sulfate, filtered, and evaporated in vacuo to give 1-bromo-5,6-epoxy-6-methyl-undecan-2-one (10.63 g).

IR (neat): 1724 cm$^{-1}$ (CO of ketone);
NMR (CDCl$_3$) δ3.90 (s, 2H, —CO—CH$_2$—Br), 2.78 (q, 2H, —CO—CH$_2$—CH$_2$—), 2.7 (m, 1H, C$_5$—H), 0.92 [dist'd t, 3H, CH$_3$(CH$_2$)$_4$—].
GC/MS=two fractions (∼40/60 ratio). M$^+$ 276 not visible, M—C$_5$H$_{11}$=205, BP=83.

When in the above procedure 1-bromo-6-methyl-2-oxo-oct-5-ene and 1-bromo-6-methyl-2-oxo-non-5-ene are employed in place of 1-bromo-6-methyl-2-oxo-undec-5-ene, the corresponding 1-bromo-5,6-epoxy-6-methyl-octan-2-one and 1-bromo-6-methyl-nonan-2-one are obtained.

EXAMPLE 4

2-[2-Bromomethyl-2-hydroxy-tetrahydrofuran-5'-yl]heptan-2-ol (5)

Aqueous hydrochloric acid (0.2 N, 1.5 ml) is added to 1-bromo-5,6-epoxy-6-methyl-undecan-2-one (3.26 g, 11.8 mmole) in acetone (9.0 ml) while stirring at 0° C. After 5 minutes of stirring, the solution is kept at 0° C. for 5 days. The acetone is evaporated in vacuo, the residue is dissolved in methylene chloride, and washed with saturated sodium bicarbonate-water, then with saturated sodium chloride-water, dried with sodium sulfate, filtered, and evaporated in vacuo to give 2-[2-bromomethyl-2-hydroxy-tetrahydrofuran-5'-yl]-heptan-2-ol (3.46 g of crude hemiketal).

IR (neat): 3400 (OH), 900–1150 cm$^{-1}$ (ether bands);
NMR (CDCl$_3$) δ4.0 (m, 1H,

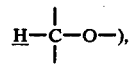

3.53 (s, 2H, —CH$_2$—Br).
GC/MS=two fractions (∼40/60 ratio), showing identical mass spectra. M$^+$ 294 not visible, [M—H$_2$O—C$_5$H$_{11}$]=205/7, BP 83.

When in the above procedure 1-bromo-5,6-epoxy-6-methyl-dodecan-2-one and 1-bromo-5,6-epoxy-6-methyl-tridecan-2-one are employed in place of 1-bromo-5,6-epoxy-6-methyl-undecan-2-one, the corresponding 2-[2-bromomethyl-2-hydroxy-tetrahydrofuran-5'-yl]-octan-2-ol and 2-[2-bromomethyl-2-hydroxy-tetrahydrofuran-5'-yl]-nonan-2-ol are obtained.

EXAMPLE 5

2-[2-Bromomethyl-2-methoxy-tetrahydrofuran-5'-yl]heptan-2-ol (6)

To 2-[2-bromomethyl-2-hydroxy-tetrahydrofuran-5'-yl]heptan-2-ol (3.46 g, 11.78 mmole) in trimethylorthoformate (4.0 ml, ∼37 mmole), methanolic sulfuric acid (2.0 ml of a solution of 0.27 ml of conc. sulfuric acid and 99.7 ml of methanol) is added while stirring at 0° C. After 15 minutes of stirring, the solution is stored at 0° C. for 48 hours and is then added dropwise to saturated aqueous sodium bicarbonate and methylene chloride, while stirring in the cold. The methylene chloride extract is washed with saturated aqueous sodium chloride, dried with sodium sulfate, filtered, and evaporated in vacuo to give crude cis and trans 2-[2-bromomethyl-2-methoxy-tetrahydrofuran-5'-yl]-heptan-2-ol (3.17 g).

NMR (CDCl$_3$) δ3.93 (m, 1H, H—C—O—), 3.53 (s, 70% of 2H, —CH$_2$—Br of cis), 3.52 (q, 30% of 2H, —CH$_2$Br of trans), 3.3 (s, 30% of 3H, —OCH$_3$), 3.23 (s, 70% of 3H, —OCH$_3$), [dist'd t, 3H, CH$_3$(CH$_2$)$_4$—].

When in the above procedure 2-[2-bromomethyl-2-hydroxy-tetrahydrofuran-5'-yl]-tetradecan-2-ol and 2-[2-bromomethyl-2-hydroxy-tetrahydrofuran-5'-yl]pentadecan-2-ol are employed in place of 2-[2-bromomethyl-2-hydroxy-tetrahydrofuran-5'-yl]-heptan-2-ol, the corresponding 2-[2-bromomethyl-2-methoxy-tetrahydrofuran-5'-yl]-tetradecan-2-ol and 2-[2-bromomethyl-2-methoxy-tetrahydrofuran-5'-yl]pentadecan-2-ol are obtained.

EXAMPLE 6

1RS,4RS,5SR-1-Methoxy-4-methyl-4-n-pentyl-3,8-dioxabicyclo[3.2.1]octane and
1RS,4SR,5SR-1-methoxy-4-methyl-4-n-pentyl 3,8-dioxabicyclo[3.2.1]octane (7)

KOH pellets (7.1 g, 0.13 mole) are added to the mixture of cis and trans 2-[2-bromomethyl-2-methoxy-tetrahydrofuran-5'-yl]-heptan-2-ol (3.02 g, 9.8 mmole) in dimethylsulfoxide (25 ml) within 5 minutes, while stirring at +21° C. under nitrogen. It is then heated to +28° C., and the stirring is continued for 10 days at this temperature.

The mixture is then cooled to room temperature; methylene chloride (100 ml) is added and the mixture is filtered through celite on a sintered glass funnel. The filtrate is washed with water, then with saturated aqueous sodium chloride, dried with sodium sulfate, filtered, and evaporated in vacuo at +25° C., then at +45° C. at 0.5 mm for 16 hours to give an oily residue (2.05 g). The residue is chromatographed on SilicAR CC-7 (200 g). Elution with chloroform affords the bicyclic ketals, 1RS,4RS,5SR-1-methoxy-4-methyl-4-n-pentyl-3,8-dioxabicyclo[3.2.1]octane and 1RS,4SR,5SR-1-methoxy-4-methyl-4-n-pentyl-3,8-dioxabicyclo[3.2.1]octane (959 mg) as the faster moving component.

IR (neat): 1020-1130 cm$^{-1}$ (ether bands);

NMR (CDCl$_3$) δ3.93 (m, 1H, H—C—O), 3.73 (m, 2H, OCH$_2$—C—O), 3.43 (s, 3H, OCH$_2$), 1.97 (m, 4H, —CH$_2$CH$_2$—), 1.07 (s, 3H, CH$_3$—C—O—), 0.95 [dist'd t, 3H, CH$_3$(CH$_2$)$_4$—].

The slower component of the column chromatography is the trans bromo-hydroxy ketal, 2-[2-bromomethyl-2-methoxy-tetrahydrofuran-5'-yl]-heptan-2-ol (860 mg).

IR (neat): 3400 (OH), 900-1150 cm$^{-1}$ ether bands);

NMR (CDCl$_3$) δ4.0 (m, 1H, H—C—O), 3.5 (q, 2H, —CH$_2$—Br), 3.33 (s, 3H, OCH$_3$), 0.90 [dist'd t, 3H, CH$_3$(CH$_2$)$_4$—].

GC/MS M$^+$ 308 not visible, M—OCH$_3$=277, BP 83.

When in the above procedure 2-[2-bromomethyl-2-methoxy-tetrahydrofuran-5'-yl]-hexan-2-ol and 2-[2-bromomethyl-2-methoxy-tetrahydrofuran-5'-yl]-butan-2-ol are employed in place of 2-[2-bromomethyl-2-methoxy-tetrahydrofuran-5'-yl]-heptan-2-ol, the corresponding 1RS,4RS,5SR and 1RS,4SR,5SR-1-methoxy-4-butyl-4-methyl-3,8-dioxabicyclo[3.2.1]octane and 1RS,4RS,5SR and 1RS,4SR,5SR-1-methoxy-4-ethyl-4-methyl-3,8-dioxabicyclo-[3.2.1]octane are obtained.

EXAMPLE 7

1RS,4RS,5SR-1-Hydroxy-4-methyl-4-n-pentyl-3,8-dioxabicyclo[3.2.1]octane and
1RS,4SR,5SR-1-hydroxy-4-methyl-4-n-pentyl-3,8-dioxabicyclo[3.2.1]octane (8)

2 N Aqueous hydrochloric acid (2 ml) is added to the bicyclic methoxy ketals, 1RS,4RS,5SR-1-methoxy-4-methyl-4-n-pentyl-3,8-dioxabicyclo[3.2.1]octane and 1RS,4SR,5SR-1-methoxy-4-methyl-4-n-pentyl-3,8-dioxabicyclo[3.2.1]octane (315 mg, 1.38 mmole) in acetone (2 ml) and the mixture is stirred at +20° C. for 48 hours. The acetone is evaporated in vacuo, and the residue is dissolved in methylene chloride, washed with saturated aqueous sodium chloride, dried with sodium sulfate, filtered and evaporated in vacuo to give 1RS,4RS,5SR-1-hydroxy-4-methyl-4-n-pentyl-3,8-dioxabicyclo[3.2.1]octane and 1RS,4SR,5SR-1-hydroxy-4-methyl-4-n-pentyl-3,8-dioxabicyclo[3.2.1]octane (259.9 mg; 88%, 60/40 mixture of C$_4$ epimers).

IR (CCl$_4$) 3600 and 3200-3500 (OH), 1720 (CO), 1050-1260 cm$^{-1}$ (ether bands).

NMR (CDCl$_3$) δ3.93 (m, 1H, H—C—O), 3.5 (2×q, —O—CH$_2$—C—OH), 1.33 (s, 60% of 3H, CH$_3$—C—O), 1.03 (s, 40% of 3H, CH$_3$—C—O), 0.9 [dist'd t, 3H, CH$_3$(CH$_2$)$_4$—].

The bicyclic hemi-ketal (4.1 g) is chromatographed on SilicAr CC-7 (196 g) using 5% ether-methylene chloride as the eluent. The earlier eluting fractions give the hemi-ketal 1RS,4SR,5SR-1-hydroxy-4-methyl-4-n-pentyl-3,8-dioxabicyclo[3.2.1]octane (353 mg), followed by a 1:1 mixture of epimers (1.57 g) and then the 1RS,4RS,5SR-1-hydroxy-4-methyl-4-n-pentyl-3,8-dioxabicyclo[3.2.1]octane (1.2 g) in the later eluting fractions.

1RS,4RS,5SR—hemi-ketal, NMR (CDCl$_3$) δ1.33 (s, 3H, CH$_3$C—O), 3.5 (q, OCH$_2$C—OH).

1RS,4SR,5SR—hemi-ketal, NMR (CDCl$_3$) δ1.03 (s, 3H, CH$_3$—C—O), 3.5 (q, OCH$_2$C—OH).

When in the above procedure 1RS,4RS,5SR-1-methoxy-4-methyl-4-n-propyl-3,8-dioxabicyclo[3.2.1]octane and 1RS,4SR,5SR-1-methoxy-4-methyl-4-n-propyl-3,8-dioxabicyclo[3.2.1]octane are employed in place of 1RS,4RS,5SR-1-methoxy-4-methyl-4-n-pentyl-3,8-dioxabicyclo[3.2.1]octane and 1RS,4SR,5SR-1-methoxy-4-methyl-4-n-pentyl-3,8-dioxabicyclo[3.2.1]octane, the corresponding 1RS,4RS,5SR-1-hydroxy-4-methyl-4-n-propyl-3,8-dioxabicyclo[3.2.1]octane and 1RS,4SR,5SR-1-hydroxy-4-methyl-4-n-propyl-3,8-dioxabicyclo[3.2.1]octane are obtained.

EXAMPLE 8

1RS,4SR,5RS-4-Methyl-4-n-pentyl-3,8-dioxabicyclo[3.2.1]octane-1-acetic acid, ethyl ester (9)

A mixture of 1RS,4RS,5SR-1-hydroxy-4-methyl-4-n-pentyl-3,8-dioxabicyclo[3.2.1]octane (647 mg, 3.02 mmole) and (carbethoxymethylene)triphenylphosphorane (2.10 g, 6.02 mmole) is heated to 90° C. for 3 days under nitrogen. After adding 50 ml of petroleum ether, the resulting suspension is refluxed for 30 minutes, and then filtered. The petroleum ether is evaporated in vacuo, and the crude residue (750 mg) is chromatographed on SilicAR CC-7 (40 g). The column is eluted with 10% ethyl ether in methylene chloride to give 1RS,4SR,5RS-4-methyl-4-n-pentyl-3,8-dioxabicyclo[3.2.1]octane-1-acetic acid, ethyl ester (400 mg, 46%) as a light yellow oil.

When in the above procedure 1RS,4RS,5SR-1-hydroxy-4-methyl-4-n-propyl-3,8-dioxabicyclo[3.2.1]octane and 1RS,4RS,5SR-4-ethyl-1-hydroxy-4-methyl-3,8-dioxabicyclo[3.2.1]octane are employed in place of 1RS,4RS,5SR-1-hydroxy-4-methyl-4-n-pentyl-3,8-dioxabicyclo[3.2.1]octane, the corresponding 1RS,4SR,5RS-4-methyl-4-n-propyl-3,8-dioxabicyclo[3.2.1]octane-1-acetic acid, ethyl ester and 1RS,4SR,5RS-4-ethyl-1-4-methyl-3,8-dioxabicyclo[3.2.1]octane-1-acetic acid, ethyl ester are obtained.

EXAMPLE 9

1RS,4RS,5RS-4-Methyl-4-n-pentyl-3,8-dioxabicyclo[3.2.1]octane-1-acetic acid, ethyl ester (10)

When in the above procedure 1RS,4SR,5SR-1-hydroxy-4-methyl-4-n-pentyl-3,8-dioxabicyclo[3.2.1]octane (350 mg) and (carbethoxymethylene)triphenylphosphorane (1.8 g) is refluxed in xylene (10 ml) for two days, 1RS,4RS,5RS-4-methyl-4-n-pentyl-3,8-dioxabicyclo[3.2.1]octane-1-acetic acid ethyl ester (470 mg, 96%) is obtained as a light yellow oil.

When in the above procedure 1RS,4SR,5SR-1-hydroxy-4-methyl-4-n-propyl-3,8-dioxabicyclo[3.2.1]octane and 1RS,4SR,5SR-4-ethyl-1-hydroxy-4-methyl-3,8-dioxabicyclo[3.2.1]octane are employed in place of 1RS,4SR,5SR-1-hydroxy-4-methyl-4-n-pentyl-3,8-dioxabicyclo[3.2.1]octane, the corresponding 1RS,4RS,5RS-1-hydroxy-4-methyl-4-n-propyl-3,8-dioxabicyclo[3.2.1]octane-1-acetic acid, ethyl ester and 1RS,4RS,5RS-4-ethyl-1-hydroxy-4-methyl-3,8-dioxabicyclo[3.2.1]octane-1-acetic acid, ethyl ester are obtained.

EXAMPLE 10

1RS,4SR,5RS-4-Methyl-4-n-pentyl-3,8-dioxabicyclo[3.2.1]octane-1-acetic acid (II)

2 N Sodium hydroxide in water (5 ml) is added to 1RS,4SR,5RS-4-methyl-4-n-pentyl-3,8-dioxabicyclo[3.2.1]-octane-1-acetic acid, ethyl ester (860 mg, 3.0 mmole) in methanol (5 ml) while stirring at 0° C. within 2 minutes. The mixture is allowed to come to 20° C. and stirring is continued for 3 days under nitrogen. The solvent is evaporated in vacuo, and the residue is extracted with methylene chloride. The methylene chloride solution is extracted with water and then with sodium chloride-water. The basic, aqueous solution is carefully acidified with 2 N hydrochloric-water (5.0 ml). The cloudy solution is extracted with methylene chloride, and the extract is washed with water and with sodium chloride-water, dried with sodium sulfate and filtered through celite on a sintered glass funnel to give 1RS,4SR,5RS-4-methyl-4-n-pentyl-3,8-dioxabicyclo[3.2.1]octane-1-acetic acid (762.7 mg).

IR (CHCl$_3$) 3100–3600, 2400–2600 (OH), 1750 and 1715 (CO of acid).

NMR (CDCl$_3$) $\delta$3.88 (t, 1H, —O—C$\underline{H}$—CH$_2$—), 3.60 (q, 2H, —O—C$\underline{H}_2$—C—O), 2.63 (br s, 2H, —C$\underline{H}_2$—CO$_2$H), 1.92–2.08 (m, 4H, —C$\underline{H}_2$—C$\underline{H}_2$—), 1.33 (s, 3H, C$\underline{H}_3$—C—O—), 0.88 [dist'd t, 3H, C$\underline{H}_3$(CH$_2$)$_4$—].
M$^+$ 328, M—CH$_3$=313, M—H$_2$O=310, M—C$_5$H$_{11}$=257, M—TMS—OH=238; BP=73.

When in the above procedure 1RS,4SR,5RS-4-methyl-4-propyl-3,8-dioxabicyclo[3.2.1]octane-1-acetic acid, ethyl ester and 1RS,4SR,5RS-4-n-hexyl-4-methyl-3,8-dioxabicyclo[3.2.1]-octane-1-acetic acid, ethyl ester are employed in place of 1RS,4SR,5RS-4-methyl-4-n-pentyl-3,8-dioxabicyclo[3.2.1]-octane-1-acetic acid, ethyl ester, the corresponding 1RS,4SR,5RS-4-methyl-4-propyl-3,8-dioxabicyclo[3.2.1]octane-1-acetic acid and 1RS,4SR,5RS-4-n-hexyl-4-methyl-3,8-dioxabicyclo[3.2.1]-octane-1-acetic acid are obtained.

EXAMPLE 11

1RS,4RS,5RS-4-methyl-4-n-pentyl-3,8-dioxabicyclo[3.2.1]octane 1-acetic acid (11)

Following the procedure of Example 9, to 1RS,4RS,5RS-4-methyl-4-n-pentyl-3,8-dioxabicyclo[3.2.1]-octane-1-acetic acid, ethyl ester (470 mg, 1.65 mm) in methanol (5 ml) is added while stirring at 0° C. under nitrogen 2 N NaOH—H$_2$O (5 ml). The mixture is then stirred at +20° C. for three days under nitrogen. The solvent is evaporated in vacuo, and the residue extracted with methylene chloride. The basic, aqueous solution is carefully acidifed with 2 N HCl—H$_2$O, extracted with methylene chloride, washed with water and with NaCl—H$_2$O, dried with Na$_2$SO$_4$, filtered, and evaporated to give 1RS,4RS,5RS-4-methyl-4-n-pentyl-3,8-dioxabicyclo[3.2.1]octane-1-acetic acid (210 mg, 50.0%). IR (neat) 3100–3600, 2600–2900 (OH), 1748 and 1715 cm$^{-1}$ (CO of acid). NMR (CDCl$_3$)$\delta$: 3.90 (t, 1H, —O—C$\underline{H}$—CH$_2$), 3.56 (q, 2H, —O—C$\underline{H}_2$—C—O), 2.63 (s, —C$\underline{H}_2$—CO$_2$H), 1.03 (s, 3H, CH$_3$—C—O—), 0.9 [distd. t, 3H, C$\underline{H}_3$(CH$_2$)$_4$—]. GC/MS of TMS derivative; M+ =328; BP=73.

EXAMPLE 12

2RS,3SR- and 2RS,3RS-3-Hydroxy-6-methoxyimino-2-methyl-2-n-pentyl-oxepane (12)

Anhydrous potassium acetate (68.6 mg, 0.7 mM) is added to a mixture of 1RS,4RS,5SR and 1RS,4SR,5SR-1-hydroxy-4-methyl-4-n-pentyl-3,8-dioxabicyclo[3.2.1]octane (106.0 mg, 0.49 mM) in methanol (1.0 ml) while stirring at +21° C. Methoxyamine hydrochloride (64.0 mg, 0.65 mM) is added to this solution and stirring is continued for four days under nitrogen. The methanol is evaporated in vacuo and the residue dissolved in methylene chloride. The solution is washed with water, dried with Na$_2$SO$_4$, filtered and evaporated in vacuo to give 2RS, 3SR- and 2RS,3RS-3-hydroxy-6-methoxyimino-2-methyl-2-n-pentyloxepane (109.1 mg, 91.6%) NMR (CDCl$_3$)$\delta$: 3.80, 3.77 (2$\times$s, 3H total, 40/60=N—OCH$_3$), 3.57 (m, 1H, —C$\underline{H}$OH); IR (neat) 2975 (OH), 1630 (=NOCH$_3$), 1150 and 1100 cm$^{-1}$ (ether CO). GC/MS=two fractions (40/60 ratio. M+ 243 not visible, M—CH$_2$CHOH=199, BP 128).

EXAMPLE 13

2RS,3SR- and 2RS,3RS-3-acetoxy-6-methoxyimino-2-methyl-2-n-pentyl-oxepane (13)

A mixture of pyridine (0.6 ml) and acetic anhydride (0.3 ml) is added to 2RS,3SR- and 2RS,3RS-3-hydroxy-6-methoxyimino-2-methyl-2-n-pentyl-oxepane (53.2 mg, 0.2 mM) at 21° C. After stirring under nitrogen at 21° C. for sixteen hours the system is evaporated in vacuo. The residue is dissolved in methylene chloride, washed with saturated NaCl/H$_2$O containing a few drops of 2 N HCl (pH 2.0). It is then washed with NaCl/H$_2$O, dried with Na$_2$SO$_4$, filtered, and evaporated in vacuo to give 2RS,3SR- and 2RS-3RS-3-acetoxy-6-methoxyimino-2-methyl-2-n-pentyl-oxepane (53.3 mg, 93.5%). IR (neat): 1750 (CO of acetate), 1630 (—C=NOCH$_3$), 1250 (acetate), 1150, 1100 and 1050 cm$^{-1}$ (ether bands). NMR (CDCl$_3$) $\delta$4.82 (m, 0.6 H, ax H of —C$\underline{H}$OAc), 4.47 (m, 0.4 H, eq H of —C$\underline{H}$OAc), 3.87, 3.83 (2$\times$s, 3H, =NOC$\underline{H}_3$), 2.13, 2.10 (2$\times$s, 3H, —O—CO—C$\underline{H}_3$).

EXAMPLE 14

2RS,3SR- and 2RS,3RS-3-Acetoxy-2-methyl-2-n-pentyl-oxepan-6-one (60/40 isomer ratio) (14a and 14b)

The acetoxy oxime-ether (53.0 mg, 0.19 mm) obtained in Example 13 above in acetone (7.6 ml) and 2 N aqueous hydrochloric acid (0.4 ml) is stirred and refluxed under nitrogen for three hours. The mixture is evaporated in vacuo and the residue is dissolved in CH$_2$Cl$_2$. The solution is washed with saturated NaCl/H$_2$O containing a few drops of NaHCO$_3$/H$_2$O to make it basic, then with NaCl/H$_2$O, dried with Na$_2$SO$_4$, filtered, and evaporated in vacuo to give 43.8 mg (90%) of a mixture. The mixture is dissolved in 0.5 ml of methylene chloride and applied to one 20$\times$20$\times$0.1 cm silica gel plate with fluorescent indicator (analab) using 10% ether in methylene chloride developing mixture to give 25.4 mg (73%) of the keto acetate in the form of the C-3 isomers, as indicated by nmr spectroscopy. NMR (CDCl$_3$)$\delta$: 4.9 (m, 1H, —C$\underline{H}$OAc), 4.08 (s, 2H, —O—CH$_2$—CO—), 2.1, 2.07 (2$\times$s, 3H, —OCOC$\underline{H}_3$), 1.25, 1.17 (2$\times$s, 3H,

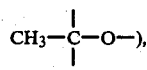

0.90 [distd. t, 3H, C$\underline{H}_3$(CH$_2$)$_4$].

We claim:

1. The process for the preparation of compounds of the formula:

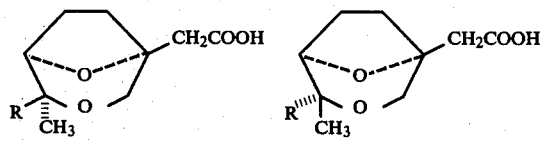

which comprises reacting a compound of the formula:

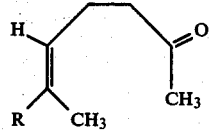

with lithium diisopropylamide followed by reaction of the intermediate with trimethylsilyl chloride to form a silyl enol ether of the formula:

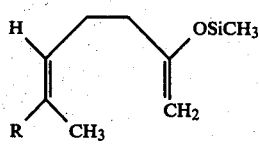

reacting the enol ether with N-bromosuccinimide to form a bromide of the formula:

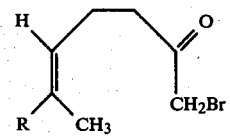

reacting the bromide with a peracid to form an epoxide of the formula:

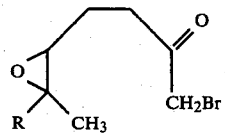

reacting the epoxide with an acid to form a hemi-ketal of the formula:

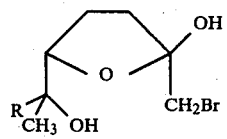

reacting the hemi-ketal with a trialkylorthoformate to form a ketal of the formula:

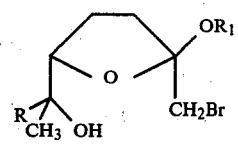

reacting the ketal with a cyclizing agent to form an oxido oxepane of the formula:

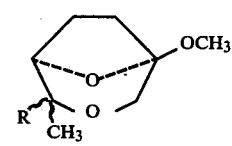

reacting the oxido oxepane with dilute acid to give a mixture of epimeric hemi-ketals of the formula:

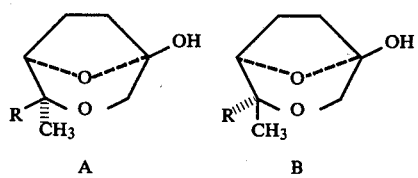

separating the epimers by physical means and i. reacting Compound A with a carbalkoxymethylenetriphenylphosphorane to form an ester of the formula:

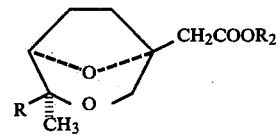

and hydrolyzing the ester with a base; and ii. reacting Compound B with a carbalkoxymethylenetriphenylphosphorane to form an ester of the formula:

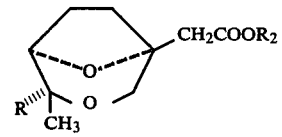

and hydrolyzing the ester with a base, wherein R is a straight or branched chain alkyl group having 1–12 carbon atoms and R$_1$ and R$_2$ are lower alkyl having 1–5 carbon atoms.

2. The process of claim 1 wherein the acid is hydrochloric acid.

3. The process of claim 1 wherein the cyclizing agent is potassium hydroxide.

4. The process of claim 1 wherein the carbalkoxymethylene triphenylphosphorane is carbethoxymethylenetriphenylphosphorane.

5. The process of claim 1 wherein the base is potassium hydroxide.

6. The process according to claim 1 wherein the dilute acid is selected from hydrochloric acid, sulfuric acid and acetic acid.

7. The process of claim 1 wherein the peracid is m-chloroperbenzoic acid.

8. The process of claim 1 wherein the trialkylorthoformate is trimethylorthoformate.

9. The process for the preparation of compounds of the formula

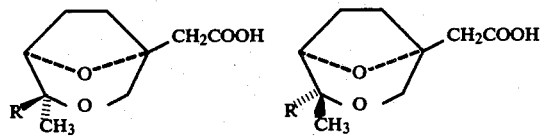

which comprises reacting a ketal of the formula:

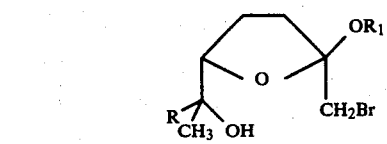

with a cyclizing agent to form an oxido-oxepane of the formula:

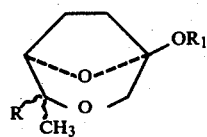

reacting the oxido-oxepane with dilute acid to give a mixture of epimeric hemi-ketals of the formula:

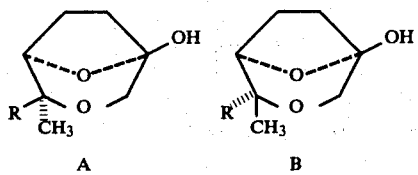

separating the epimers by physical means and i. reacting Compound A with a carbalkoxymethylenetriphenylphosphorane to form an ester of the formula:

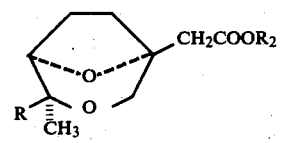

and hydrolyzing the ester with a base; and ii. reacting Compound B with a carbalkoxymethylene triphenylphosphorane to form an ester of the formula:

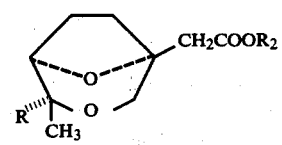

and hydrolyzing the ester with a base, wherein R is a straight or branched chain alkyl group having 1-12 carbon atoms and $R_1$ and $R_2$ are lower alkyl having 1-5 carbon atoms.

10. The process of claim 9 wherein the cyclizing agent is potassium hydroxide.

11. The process of claim 9 wherein thee carbalkoxymethylene triphenylphosphorane is carbethoxymethylenetriphenylphosphorane.

12. The process of claim 9 wherein the base is sodium hydroxide.

13. The process of claim 9 wherein the dilute acid is selected from hydrochloric acid, sulfuric acid and acetic acid.

* * * * *